United States Patent
Sreedharan et al.

(10) Patent No.: US 11,911,302 B2
(45) Date of Patent: Feb. 27, 2024

(54) SELF EXPANDING FLOW DIVERSION DEVICE WITH ENHANCED KINK RESISTANCE AND RADIAL STRENGTH

(71) Applicant: SREE CHITRA TIRUNAL INSTITUTE FOR MEDICAL SCIENCES AND TECHNOLOGY, Thiruvananthapuram (IN)

(72) Inventors: Sujesh Sreedharan, Thiruvananthapuram (IN); Anku Sreekumar, Thiruvananthapuram (IN); Sreehari Unnikrishnan Nair, Thiruvananthapuram (IN)

(73) Assignee: SREE CHITRA TIRUNAL INSTITUTE FOR MEDICAL SCIENCES AND TECHNOLOGY

( * ) Notice: Subject to any disclaimer, the term of this patent is extended or adjusted under 35 U.S.C. 154(b) by 344 days.

(21) Appl. No.: 17/285,771

(22) PCT Filed: Dec. 19, 2019

(86) PCT No.: PCT/IN2019/050936
§ 371 (c)(1),
(2) Date: Apr. 15, 2021

(87) PCT Pub. No.: WO2020/136672
PCT Pub. Date: Jul. 2, 2020

(65) Prior Publication Data
US 2021/0386566 A1    Dec. 16, 2021

(30) Foreign Application Priority Data
Dec. 28, 2018    (IN) .............................. 201841049649

(51) Int. Cl.
*A61F 2/90* (2013.01)
*A61F 2/06* (2013.01)
*A61F 2/82* (2013.01)

(52) U.S. Cl.
CPC .................. *A61F 2/90* (2013.01); *A61F 2/06* (2013.01); *A61F 2002/068* (2013.01);
(Continued)

(58) Field of Classification Search
CPC ...... A61F 2/90; A61F 2/82; A61F 2/06; A61F 2/852; A61F 2250/0039; A61F 2250/0098; A61F 2002/068
See application file for complete search history.

(56) References Cited

U.S. PATENT DOCUMENTS

| | | | |
|---|---|---|---|
| 6,342,068 B1 | 1/2002 | Thompson | |
| 2012/0191178 A1* | 7/2012 | Laduca | A61F 2/915 623/1.16 |

(Continued)

FOREIGN PATENT DOCUMENTS

| | | |
|---|---|---|
| EP | 2946750 | 11/2015 |
| WO | 2018163056 | 9/2018 |

OTHER PUBLICATIONS

International Search Report and Written Opinion for International Application No. PCT/IN2019/050936, dated Jul. 2, 2020.

*Primary Examiner* — Dinah Baria
(74) *Attorney, Agent, or Firm* — Dinsmore & Shohl LLP

(57) ABSTRACT

A flow diverter device is used to redirect the blood flow inside the cerebral blood vessels and for the reduction of blood flow to the aneurysm, hence preventing the chance of aneurysm rupture as well as promoting the healing of the aneurysm. The novel design of the device, using a set of thicker wires, provides high kink resistance and radial strength. Two patterns of inter-braiding the thicker set of wires with the finer braid are disclosed, one having a
(Continued)

checker-board and the other a ring structure. Both patterns are highly kink resistant with the checker-board design providing minimal loss in flexibility, whereas the ring design provides greater radial strength. The device could be made of super elastic materials like Nitinol wires with the thicker set being radio opaque. The device is highly kink resistant and sufficiently flexible for use in vasculature with complex bends.

8 Claims, 2 Drawing Sheets

(52) U.S. Cl.
CPC . *A61F 2002/823* (2013.01); *A61F 2250/0039* (2013.01); *A61F 2250/0098* (2013.01)

(56) References Cited

U.S. PATENT DOCUMENTS

| | | | |
|---|---|---|---|
| 2015/0081000 A1* | 3/2015 | Hossainy | A61F 2/88 623/1.2 |
| 2018/0245745 A1 | 8/2018 | Tousain et al. | |

* cited by examiner

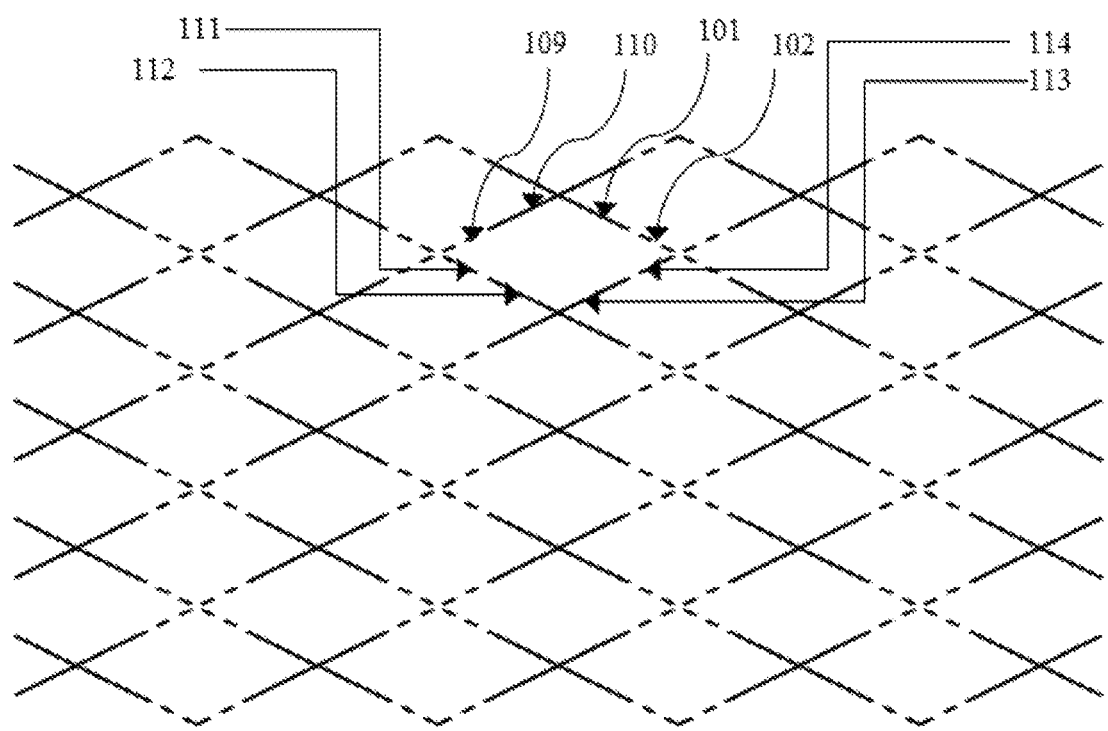
Fig: 1.
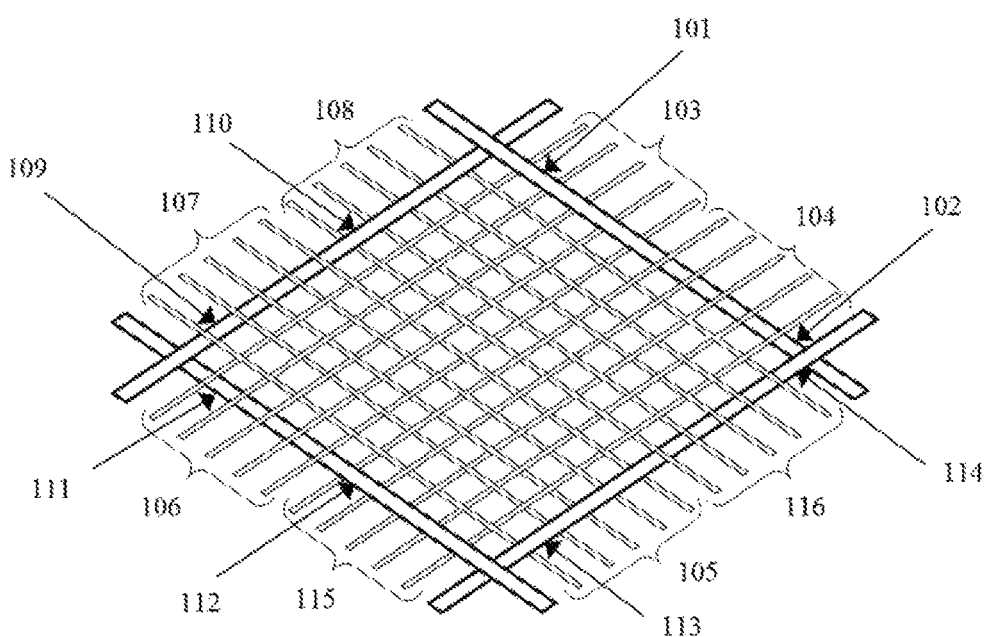
Fig: 1A.

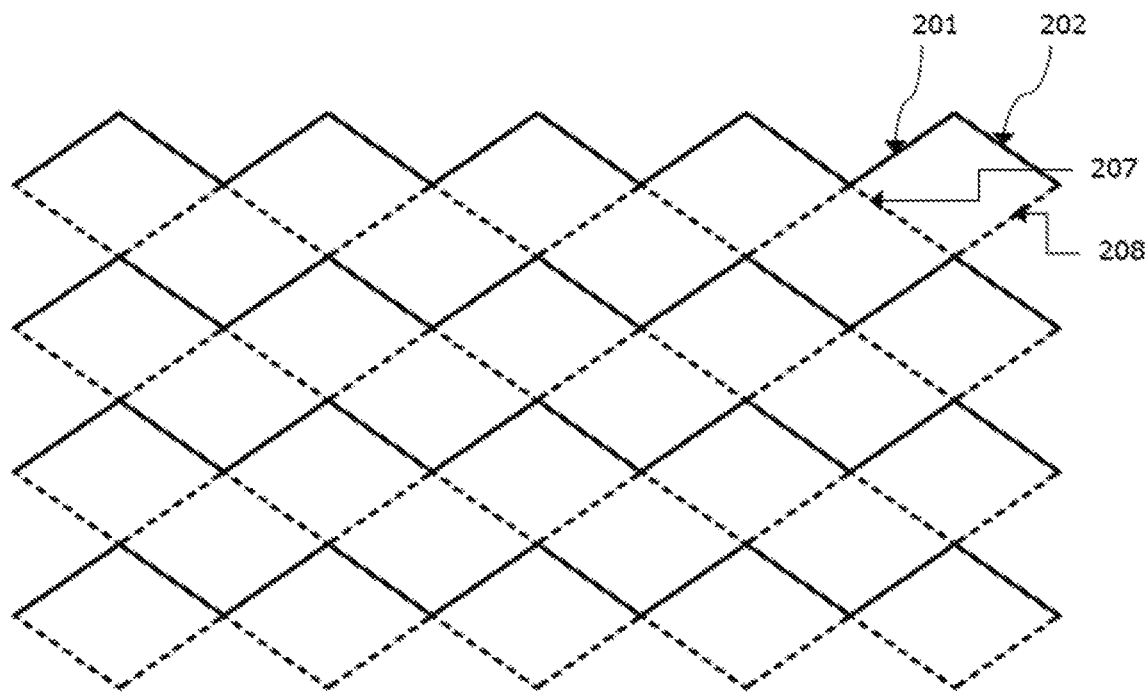
Fig: 2.
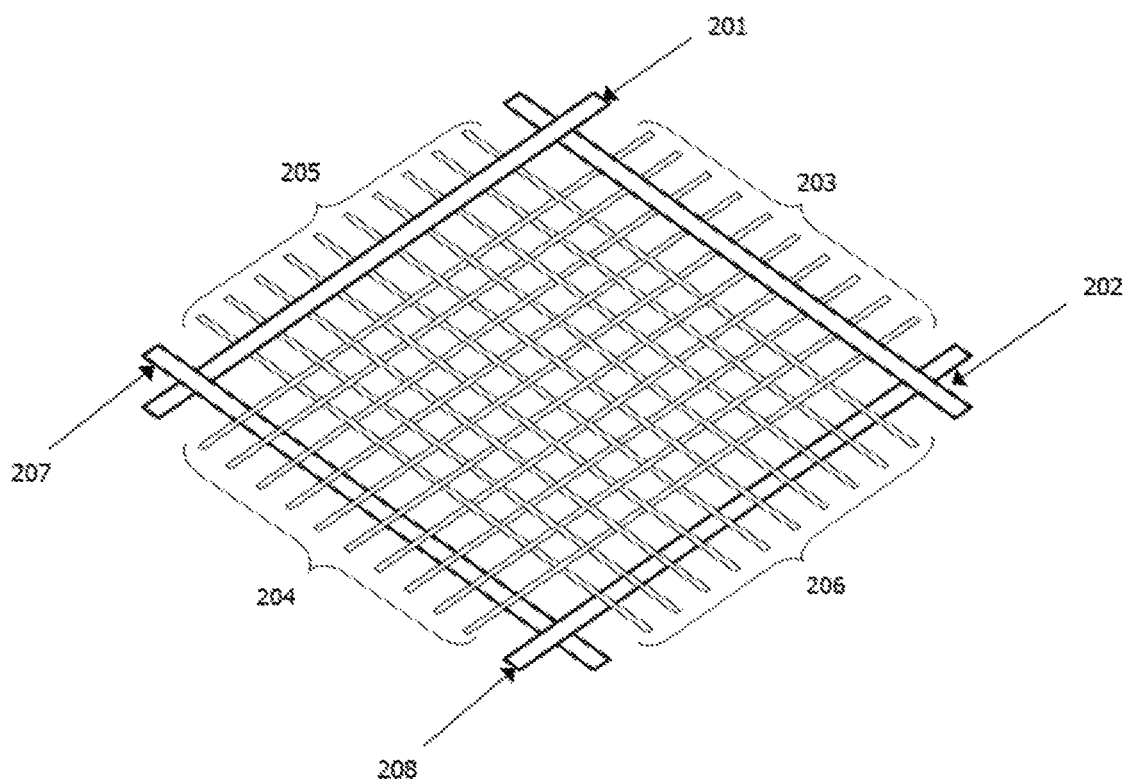
Fig: 2A.

SELF EXPANDING FLOW DIVERSION DEVICE WITH ENHANCED KINK RESISTANCE AND RADIAL STRENGTH

FIELD OF INVENTION

The present invention relates to a self expanding flow diversion device with enhanced kink resistance and radial strength. More particularly the present invention relates to a intravascular medical device called as a self expanding flow diverter employed for diverting the flow within the parent vessel itself.

BACKGROUND OF THE INVENTION

The term intracranial aneurysm refers to any localized ballooning or dilation of an artery in the brain. Since the wall of the dilated portion in the vessel experiences continuous blood flow, the inner muscles of the vessel (intima) can weaken progressively increasing the probability of aneurysm rupture resulting in a hemorrhagic stroke, which could be severely debilitating and fatal. So flow diversion is essential for rectifying such issues.

The patent document US0021816A1 (2007) describes that intracranial aneurysm is initiated and developed by hemodynamic interactions between blood flow and vessel wall. An abnormal dilation of an artery in the brain that results from the weakening of the inner muscular layer of a blood vessel wall forms an intracranial aneurysm. The vessel forms a blister, saccular or round berry shaped dilation that can become thin and rupture without warning. The resultant bleeding into the space around the brain is called a subarachnoid hemorrhage (SAH). This kind of hemorrhage can lead to a stroke, coma and/or death.

In India, the cumulative incidence of stroke ranged from 105 to 152/100,000 persons per year, and the crude prevalence of stroke ranged from 44.29 to 559/100,000 persons in different parts of the country during the past decade. The surgical approach to treat cerebral aneurysms is craniotomy, in which a bone flap is temporarily removed from the skull to access the brain and a clip is placed in the neck of aneurysm, so that it is excluded from the main flow.

The aneurysm clip was introduced by Dandy in 1936. In 1990s, this tedious process was replaced by modern endovascular techniques. A majority of these techniques involve placement of coils, especially platinum, or placing liquid polymer of high viscosity inside the aneurysm by means of a high pressure microcatheter. These techniques are less invasive and cost effective when compared to craniotomy. Although the coiling is beneficial it has a few limitations: they can only be used for only small neck aneurysms which can hold the coil inside the aneurysm and the second risk factor is rupture of aneurysm while placing the coil within extreme thin walled aneurysm. The third risk factor is that the coil may not fully fill the volume of aneurysm, since the ones deployed first may interfere with the deployment of the later ones. In the prior art US0125053 A1 (2009), discloses the introduction of liquid polymer into the aneurysm, but the potential consequences of high viscous fluid and time dependent solidification and clogging are unknown, and it has not been approved by US FDA.

The patent US0249620 A1 (2014) discusses about the usage of a combination of detachable coils and stents in case of wide neck aneurysms. Stents are used for holding the coil inside the aneurysm if the neck of the aneurysm is large preventing slippage of the coil from aneurysm into parent vessel. Also the stent helps to keep the parent vessel open. However, the main disadvantage is that this procedure takes a long duration along with risk of perforation and incomplete filling of the aneurysm. The patent US0021816A1 (2007) describes about a case with change in blood flow pattern after coiling and stenting. Flow pattern and wall stress fields are factors which play a crucial role in the healing of aneurysm after the endovascular procedure.

Over the past decade, many studies have shown that redirection of the blood flow away from the aneurysm within the parent artery can heal the aneurysm without any risk of damage to the aneurysm wall. Flow diverter stents are the class of devices that divert flow away from the aneurysm and into the parent blood vessel, thus reducing chances of aneurysm rupture and promoting its healing. It can be manufactured from metal or polymer wires of different diameters braided together to form a tubular mesh. The pores in the mesh are made fine enough to block the blood flow into the aneurysm. The flow diverter can be radially compressed during delivery and can be expanded in radial direction during deployment within the arterial lumen.

In the intracranial circulation, the vascular structures are extremely tortuous compared to other parts of the body. There are no significant surrounding soft tissues which support the arteries. It is very difficult to straighten the arterial wall since it is extremely thin. Straightening of the artery leads to kinks which result in flow reduction, thrombosis or direct arterial tear. Therefore the flow diverter should be flexible and adaptable to the tortuosity of the vessel boundaries without kinking.

OBJECTS OF THE INVENTION

Therefore, it is an object of the invention to propose a self expanding flow diversion device with enhanced kink resistance and radial strength which is capable of adapting to the curves and bends in cerebral arteries without kinking and reduction of cross-sectional area throughout the flow diverter lumen preserving blood flow within the blood vessel.

Another object of the invention is to propose a self expanding flow diversion device with enhanced kink resistance and radial strength which is able to enhance radial force to adhere to the walls of the parent artery of complex shapes to scaffold the artery and to divert the blood away from the aneurysm with lesser chances of migration.

A still another object of the invention is to propose a self expanding flow diversion device with enhanced kink resistance and radial strength that includes several radio-opaque wires to enhance radio-opacity of the device causing the device to be visualized during the endovascular procedure.

SUMMARY OF THE INVENTION

The present invention is flow diverter stent braided using two sets of elastic wires (such as of Nitinol or CoCr alloys) in which the second set has thicker wires with higher stiffness. The two sets of wires are braided together with the second set braided in either a checker-board pattern or a ring pattern. This novel braid pattern gives enhanced kink resistance and better radial strength to the flow diverter. Even when bent of 180° and above, the flow diverter exhibits excellent radial strength and kink resistance without reduction of area throughout the cross section of the flow diverter. Additionally the thicker set of wires could include radio-opaque wires for better visibility.

The two patterns of the present invention differ in that the checker-board pattern has a greater flexibility whereas the ring pattern has a greater radial strength.

BRIEF DESCRIPTION OF THE ACCOMPANYING DRAWINGS

FIG. 1: shows the unfolded structure of the invented device with checker-board pattern.

FIG. 1A: shows the unit cell of the checker-board pattern.

FIG. 2: shows the unfolded structure of another embodiment of the invented device with ring pattern.

FIG. 2A: shows the unit cell of the ring pattern.

DETAILED DESCRIPTION OF A PREFERRED EMBODIMENT OF THE INVENTION

The present invention of the flow diverter device has a novel braiding pattern using two sets of wires in which the second set has thicker wire with higher stiffness. The wires used for braiding could be of Nitinol, which is superelastic and can recover its shape from large strains. The invention could be manufactured by conventional braiding process using a mandrel of suitable diameter and geometry. By changing the number of wires, braid angle and thickness of the wires (stiffer wire with flexural rigidity; here after mentioned as thicker wire), the porosity can be varied as per the requirement for flow diversion. The thicker wires are braided together with the finer wires in an interleaved fashion, wherein the thicker wires passes over a multiplicity of finer wires which are braided continuously, on one side before crossing over to the other side of the finer wires.

The present invention with the checker-board pattern when unfolded and laid flat horizontally:

has braided cells containing thicker (stiffer) and finer wires, where in four thicker wires forms the boundary of the cell, which enclose and crosses the finer wire in a checker-board pattern, characterized in that for the thicker set of wires within one cell, one-half of a single thick wire is above (and the other half below) the finer set of wires, so that the crossings of the thicker wires which are X-shaped are completely on one side of the fine braid forming the checker-board pattern;

has a symmetric array of rhomboidal cells, where each cell in both the circumferential as well as axial directions, is a replication of the adjacent cell.

Another embodiment of the present invention, with the ring pattern when unfolded and laid flat horizontally:

has braided cells containing thicker (stiffer) and finer wires, where in four thicker wire forms the boundary of the cell, which enclose and crosses the finer wire in ring pattern, characterized in that the upper sides of the cell are above (and lower sides of the cell below) the finer set of wires, so that a continuous zig-zag ring of thicker wires is on one side of the fine braid forming the ring pattern;

has a symmetric array of rhomboidal cells, where each cell in both the circumferential as well as axial directions, is a replication of the adjacent cell.

In the present invention, the tubular structure of flow diverters employs two different wire diameters. The thicker wire can have a diameter of 1.5 to 4 times the diameter of the finer wire and the thicker wire overlaps the finer wire in either a checkerboard or ring pattern to achieve higher kink resistance and higher radial strength. The thicker wire resists the deformation in the cross-section of the flow diverter so that even at smaller radius of curvature better kink resistance and radial strength can be achieved. The thicker wires are lesser in number and can also be made radio-opaque or be replaced with radio opaque wires. Radio opaque materials like gold, platinum, tantalum, iridium or their alloys can be used to form these wires, and utilize methods for incorporating radio opaque materials into the flow diverter such as chemical deposition, edge coating, sputtered deposition and vapor deposition to name a few. Further these larger set of wires could be a tube of any elastic material such as nitinol and be filled with any radio-opaque material such as platinum.

The finer wires are braided so as to get a low porosity throughout the surface of the flow diverter. The reinforcement of finer diameter wires with the thicker wires provides the higher radial strength with high kink resistance throughout the cross section of the device.

The shape setting of the device for a specific configuration is done with heat treatment which is well known in the art for shape memory alloys.

Two novel patterns for inter braiding the set of thicker wires with the set of finer wires are disclosed here and termed (i) checker-board and (ii) ring. For the checker-board pattern (FIG. 1 and FIG. 1A), the thicker wire is diamond (1×1) braided and finer diameter wire is braided in a regular (2×2) pattern. Throughout the surface the thicker wire crosses above and below half the number of the finer wires inside a cell forming a checker-board pattern, and hence the name checker-board design. The said checker-board pattern and the reinforcement of thicker wires in the said pattern enhance kink resistance and minimal loss of flexibility to the invented flow diverter device. The loss of flexibility is minimized by having the crossings of the thicker wire fully on one side of the finer braid so that the sliding of the thicker wires on each other is minimally restricted.

The thick lines (101, 110, 112 and 113) show the larger diameter wire, crossing above half the number of finer wires (103, 108, 115 and 105 respectively) as in FIG. 1A. The thick dotted lines (102, 109, 111 and 114) show the larger diameter wire crossing beneath half the number of finer wires (104, 107, 106 and 116 respectively) as in FIG. 1A. Thus the checker-board pattern of the device is obtained.

In a second embodiment of the invention, another pattern (FIG. 2 and FIG. 2A) termed Ring is used, where the thicker wire is diamond braided and finer wire is braided in 2×2 pattern, and each thicker wire is crossing above and below all the finer wire in a unit cells forming a ring pattern, hence the name ring design. The said ring pattern and the reinforcement of thicker wire in the said ring pattern enhance kink resistance and radial strength to the invented flow diverter device.

The thick line (201 and 202) shows the larger diameter wire crossing above all the finer wires (203 and 205 respectively) as in FIG. 2A. The thick dotted line (207 and 208) shows the larger diameter wire crossing below all the finer wire (204 and 206) as in FIG. 2A. Thus the Ring pattern of the device is obtained. Since the finer braid and the thicker braid intersect at the crossings of the thicker wires the sliding of the thicker wires on each other is reduced leading to an increased radial strength, however at the cost of an increased loss of flexibility.

In the present invention, for both designs of the device, the thicker set is a diamond braid whereas the finer set is a regular braid. The pattern of braid within the sets could be varied to any braiding pattern such as diamond, regular or hercules.

An empirical relation for finding the number of wires used for braiding a flow diverter is:

$$N = n \times M + M$$

Where,
- M=Number of thicker wires
- n=Number of finer wires across one thicker wire within a single cell.
- N=Total number of wires used in braiding The number of wires 'n' could vary from 4 to 32 and 'M' could vary from 4 to 16. The number of wires used for braiding 'n' depends on the required porosity of the device and 'M' on the required radial strength as well as kink resistance.

The invention claimed is:

1. A self expanding flow diversion device with enhanced kink resistance and radial strength employed in an arterial lumen, the device comprising;
   a plurality of cells, each cell bounded by four thick wires, wherein each thick wire has a length, each cell having four corners, and each cell comprising of a set of fine wires braided together to form a fine braid, wherein a tubular device is formed by repeating the plurality of cells in axial as well as circumferential directions;
   each cell characterized in that,
   half the length of each thick wire (portions 101, 110, 112, 113) being disposed above the fine wires (groups 103, 105, 115, 108), and a remaining length of each thick wire (portions 102, 109, 111, 114) being disposed below the fine wires (groups 104, 107, 106, 116), such that each corner of the cell comprises an X-shaped crossing formed by two thick wires crossing one another, wherein two X-shaped crossings are formed by two thick wires which are disposed under the fine wires and two X-shaped crossings are formed by two thick wires which are disposed above the fine wires, forming a checker board pattern,
   wherein, the self expanding flow diversion device having the checker board pattern enhances the kink resistance and radial strength with minimal loss in flexibility.

2. The self expanding flow diversion device as claimed in claim 1, wherein all, or a portion of, the thick wires are radio-opaque by any of the below procedures;
   a. coating with radio-opaque materials,
   b. replacing with radio-opaque wires,
   c. replacing with tubes filled with radio-opaque material.

3. The self expanding flow diversion device as claimed in claim 1, wherein the thick wires have a diameter 1.5 to 4 times a diameter of the fine wires, and wherein the thick wires have configured to resist deformation in a cross section of the self expanding flow diversion device.

4. The self expanding flow diversion device as claimed in claim 1, wherein the fine wires are reinforced with the thick wires throughout a cross section of the self expanding flow diversion device.

5. The self expanding flow diversion device as claimed in claim 1, wherein a total number (N) of wires in the self expanding flow diversion device is:
$$N = n \times M + M$$
where,
- M=a number of the thick wires; and
- n=a number of the fine wires which cross one thick wire of a single cell.

6. A self expanding flow diversion device with enhanced kink resistance and radial strength employed in an arterial lumen, the device comprising;
   a plurality of cells, each cell bounded by four thick wires (201, 202, 207, 208) and comprising fine wires braided together to form a fine braid, wherein a tubular device is formed by repeating the plurality of cells in axial as well as circumferential directions;
   each cell characterized in that,
   upper bounds of the cell formed by two thick wires (201, 202), of the four thick wires (201, 202, 207, 208), wherein an entire length of each of the two thick wires is disposed above the fine wires (groups 205, 203), and lower bounds of the cell formed by a remaining two thick wires (207, 208), of the four thick wires (201, 202, 207, 208), wherein an entire length of each of the remaining two thick wires is disposed below the fine wires (groups 204, 206), such that the two thick wires (201, 202) and the remaining two thick wires (207, 208) each, respectively, form a continuous zig-zag circumferential ring around a circumference of the self expanding flow diversion device, thereby forming a ring pattern along a length of the self expanding flow diversion device,
   wherein, the self-expanding flow diversion device having the ring pattern enhances the kink resistance and radial strength.

7. The self expanding flow diversion device as claimed in claim 6, wherein all, or a portion of, the thick wires are radio-opaque by any of the below procedures;
   a. coating with radio-opaque materials,
   b. replacing with radio-opaque wires,
   c. replacing with tubes filled with radio-opaque material.

8. The self expanding flow diversion device as claimed in claim 6, wherein a total number (N) of wires in the self expanding flow diversion device is:
$$N = n \times M + M$$
where,
- M=a number of the thick wires; and
- n=a number of the fine wires which cross one thick wire a single cell.

* * * * *